United States Patent
Cho et al.

(10) Patent No.: US 7,975,702 B2
(45) Date of Patent: Jul. 12, 2011

(54) SYSTEM AND METHOD FOR LASER LIPOLYSIS

(75) Inventors: George E. S. Cho, Hopkinton, MA (US); Leonardo Masotti, Sesto Fiorentino (IT)

(73) Assignee: El.En. S.p.A., Calenzano (IT)

( * ) Notice: Subject to any disclaimer, the term of this patent is extended or adjusted under 35 U.S.C. 154(b) by 1542 days.

(21) Appl. No.: 11/099,216

(22) Filed: Apr. 5, 2005

(65) Prior Publication Data

US 2006/0224148 A1  Oct. 5, 2006

(51) Int. Cl.
*A61B 19/00* (2006.01)

(52) U.S. Cl. .............................. 128/898; 606/3; 606/15

(58) Field of Classification Search ............ 66/3, 13–16, 66/130; 607/88, 89, 92, 100–102; 128/898; 604/19–22

See application file for complete search history.

(56) References Cited

U.S. PATENT DOCUMENTS

| | | | |
|---|---|---|---|
| 5,102,410 A * | 4/1992 | Dressel | 606/15 |
| 5,343,543 A | 8/1994 | Novak et al. | |
| 5,495,541 A | 2/1996 | Murray et al. | |
| 5,954,710 A | 9/1999 | Paolini et al. | |
| 6,106,516 A | 8/2000 | Massengill | |
| 6,203,540 B1 | 3/2001 | Weber | |
| 6,206,873 B1 * | 3/2001 | Paolini et al. | 606/7 |
| 6,235,017 B1 | 5/2001 | Jegorov et al. | |
| 6,254,597 B1 | 7/2001 | Rizoiu et al. | |
| 6,464,694 B1 * | 10/2002 | Massengill | 606/15 |
| 6,508,813 B1 | 1/2003 | Altshuler | |
| 6,511,475 B1 | 1/2003 | Altshuler et al. | |
| 6,517,532 B1 | 2/2003 | Altshuler et al. | |
| 6,562,054 B1 | 5/2003 | Weber et al. | |

(Continued)

FOREIGN PATENT DOCUMENTS

DE  103 20 984  12/2004

(Continued)

OTHER PUBLICATIONS

DEKA Medical Electronic Laser Associated, SMARTLIPO Operative Manual, dated Feb. 19, 2001.

(Continued)

*Primary Examiner* — Ahmed M Farah
(74) *Attorney, Agent, or Firm* — Hamilton, Brook, Smith & Reynolds, P.C.

(57) ABSTRACT

A device and related method for the removal of subcutaneous adipose layers comprises a laser source; an optical fiber for conveying a laser beam emitted by the laser source; and a hollow cannula for guiding the fiber to the subcutaneous treatment area. The cannula has a curved portion at its distal end, where the curved portion can be shaped to roughly conform to the contour of the patient's body structure. In this way, laser energy from the fiber, applied to the adipose layers, is generally directed away from the lower dermis of the patient, minimizing the risk of non-reversible damage to the dermis, including skin necrosis. In another embodiment, the optical fiber is a side-firing fiber that directs the laser energy away from the dermis. In other embodiments, a radiation detector, such as a thermal or optical sensor, monitors the temperature at the surface of the skin above the treatment area to warn the operator of harmful temperatures in the lower dermis. In another embodiment, a temperature sensitive material is applied to the surface of the skin above the treatment area to warn of harmful dermal temperatures. In another embodiment, a cooling mechanism cools the surface of the skin above the treatment area to prevent damage to the dermis.

10 Claims, 4 Drawing Sheets

U.S. PATENT DOCUMENTS

| | | |
|---|---|---|
| 6,605,079 B2 | 8/2003 | Shanks et al. |
| 6,605,080 B1 | 8/2003 | Altshuler et al. |
| 6,653,618 B2 | 11/2003 | Zenzie |
| 6,663,620 B2 | 12/2003 | Altshuler et al. |
| 6,723,090 B2 | 4/2004 | Altshuler et al. |
| 6,746,473 B2 | 6/2004 | Shanks et al. |
| 7,217,265 B2 | 5/2007 | Hennings et al. |
| 7,524,316 B2 * | 4/2009 | Hennings et al. ............ 606/7 |
| 2001/0025190 A1 | 9/2001 | Weber et al. |
| 2002/0038121 A1 | 3/2002 | Rozenberg et al. |
| 2003/0167053 A1 | 9/2003 | Taufig |
| 2004/0186469 A1 | 9/2004 | Woloszko et al. |
| 2006/0265032 A1 | 11/2006 | Hennings et al. |
| 2007/0142881 A1 | 6/2007 | Hennings |
| 2007/0219540 A1 * | 9/2007 | Masotti et al. ............ 606/3 |

FOREIGN PATENT DOCUMENTS

| | | |
|---|---|---|
| DE | 103 20 984 A1 | 12/2004 |
| WO | WO 91/12774 | 9/1991 |
| WO | WO 97/37723 | 10/1997 |
| WO | WO 98/14159 | 4/1998 |
| WO | WO 99/22656 | 5/1999 |
| WO | WO 01/39834 A1 | 6/2001 |
| WO | WO 01/45580 A1 | 6/2001 |
| WO | WO 01/49194 A2 | 7/2001 |
| WO | WO 01/91827 A1 | 12/2001 |

OTHER PUBLICATIONS

Neira, Rodrigo, et al., "Fat Liquefaction: Effect of Low-Level Laser Energy on Adipose Tissue," Plastic and Reconstructive Surgery, 110(3): 912-925 (2002).

Apfelberg, David B., "Results of Multicenter Study of Laser-Assisted Liposuction," Body Contouring, 23(4): 713-719 (1996).

Goldman, Alberto, et al., "Laserlipolysis: Liposuction Using Nd-YAG Laser," Rev. Soc. Bras. Cir. Plast., 17(1): 17-26 (2002).

Badin, A.Z.D., et al., "Laser Lipolysis: Flaccidity Under Control," Aesth. Plast. Surg., 26: 335-339 (2002).

"What is Liposuction?" Liposuction Information from U.S. Food and Drug Administration: Center for Devices and Radiological Health (CDRH) website (Updated: Aug. 1, 2002).

DEKA, Medical Electronic Laser Associated, SMARTLIPO, Smartlaserline, 2 page description.

MicroGroup Brochure, pp. 6, MicroGroup, Inc., Medway, MA.

European Search Report for foreign application No. EP 08 16 2477, dated Oct. 7, 2008.

Promotional Materials for Omega Engineering, Inc., 4 pp. dated 1995.

Protest and third party submission in published application under 39 C.F.R. § 1.291 served on Jun. 17, 2008.

U.S. Office Action dated Oct. 5, 2010 for U.S. Appl. No. 11/704,710.

* cited by examiner

SYSTEM AND METHOD FOR LASER LIPOLYSIS

BACKGROUND OF THE INVENTION

The reduction of subcutaneous adipose layers constitutes one of the most important areas of aesthetic treatments. A number of techniques currently exist for this purpose. One common technique, known as liposuction, consists of introduction into the adipose layers of probes roughly 5 mm in diameter through holes made in the skin of the patient undergoing treatment, for suction and removal of fat. This technique has a number of disadvantages, such as the creation of a lack of homogeneity in the form of depressions in the zone of insertion of the probe which are visible from the outside, as well as excessive bleeding of the patient undergoing treatment. Furthermore, both the cells of fat and the stroma are sucked out non-selectively.

Another technique utilizes subcutaneous ultrasonic probes to rupture the membrane of the adipose cells, thus causing the escape of liquid which then has to be sucked out subsequently. In this case, suction of the stroma is not brought about and bleeding is therefore more limited. However, the disadvantage of the lack of homogeneity of the treatment remains. Also, the probe is large and requires a large incision. Post-treatment edema can be severe, and require a long recovery time.

Still another technique, called laser lipolysis, uses energy from a laser beam to liquefy the cells of the adipose layer. The liquefied fat is then carried away naturally by the lymphatic system, or can be removed by suction. An exemplary device and method for laser lipolysis is described in U.S. Pat. No. 5,954,710 to Paolini et al., the entire teachings of which are incorporated herein by reference. As described in that patent, a hollow needle or cannula contains an optical fiber connected to a laser source. The cannula is inserted subcutaneously into a patient so that the end of the fiber comes into contact with the adipose layer. The source emits a laser beam that is conveyed by the fiber to the adipose cells, rupturing the membranes of the cells and transforming the adeps into a liquid substance which is then sucked out or preferably left in place in order to be drained by the lymphatic system and by the action of the phagocytes. In addition to a clear reduction in traumatism and greater selectivity of the method implemented in this manner in comparison with the liposuction system, an advantage is also obtained in that the energy of the laser beam can be used to cauterize the small blood vessels which may be damaged by the insertion of the needle into the adipose layers. Loss of blood is thus virtually completely eliminated.

SUMMARY OF THE INVENTION

A problem with existing systems and methods for laser lipolysis is that the laser energy emitted from the tip of the cannula can often cause undesirable damage to the skin layers above the adipose layer. This problem is particularly acute when treating body areas having a curved, contoured shape, where slight movements of the cannula tip can cause the laser energy from the tip to penetrate into the overlying dermal layers and possibly perforate the skin. In one aspect, the present invention is a device for the removal of subcutaneous adipose layers that comprises a laser source; an optical fiber for conveying a laser beam emitted by the laser source; and a hollow cannula for guiding the fiber to the subcutaneous treatment area. The cannula has a curved or bent portion at its distal end, where the curved portion can be shaped to roughly conform to the contour of the patient's body structure. In this way, laser energy from the fiber, applied to the adipose layers, is generally directed away from the lower dermis of the patient, minimizing the risk of non-reversible damage to the dermis, including skin necrosis.

In one embodiment, the laser source is an Nd:YAG laser which emits a pulsed beam having a wavelength between approximately 0.75 and 2.05 µm, preferably between about 0.8 and 1.1 µm, and an energy between about 30 and 300 mjoules per pulse. The cannula is generally between 8 and 10 inches in length, and can have an external diameter of between about 1 and 2 mm. A second "aiming" laser, which emits visible light that is coupled into the optical fiber, can be employed to assist the operator in locating the tip of the cannula underneath the patient's skin.

In another aspect, a device for the removal of subcutaneous adipose layers comprises a first laser source; an optical fiber for conveying a laser beam emitted by the first laser source; a hollow cannula for guiding the fiber; and means for preventing the laser beam emitted by the first laser source from causing non-reversible damage to the dermis of the patient. In one embodiment, the means for preventing the laser beam from causing non-reversible damage comprises a curved portion at the distal end of the cannula to direct the laser beam away from the lower dermis. In another embodiment, a side-firing fiber emits the laser beam in the opposite direction of the dermis to minimize damage to the patient's dermis.

In another embodiment, the means for preventing the laser beam from causing non-reversible damage comprises a radiation detector that is arranged to detect radiation from the surface of the skin above the tip of the fiber. The radiation detector can be, for example, a temperature sensor which detects a temperature rise in the dermis of the patient. The temperature sensor is thus able to warn the operator of potentially harmful temperatures in the underlying dermal layers. Alternatively, the radiation detector can be an optical sensor that detects the intensity of light transmitted through the patient's skin. Thus, when used in conjunction with an "aiming" laser which emits a visible laser beam from the tip of the cannula, the optical sensor can warn the operator when the cannula tip is brought into dangerously close proximity with the lower dermis of a patient.

According to yet another embodiment, the means for preventing the laser beam from causing non-reversible damage comprises a temperature sensitive material that is applied to the surface of the patient's skin above the treatment area. For example, the temperature sensitive material can be adapted to change color in response to a rise in temperature on the patient's skin, thus warning the operator of potentially harmful temperatures in the lower dermal region.

A method for the removal of subcutaneous adipose layers in accordance with the invention comprises creating an entry hole on a patient's skin; inserting a hollow cannula through the entry hole into the subcutaneous adipose layers, the cannula having a curved portion at its distal end; providing an optical fiber within the cannula, the optical fiber terminating in the vicinity of the tip of the cannula; and generating a treatment laser beam, the treatment laser beam being conveyed through the optical fiber and into the adipose layers, the wavelength and energy of the treatment beam being selected to cause rupturing of the adipose cells. The curved portion of the cannula advantageously directs the laser beam away from the lower dermis of the patient, thus minimizing serious injury to the dermal region.

In further embodiments, the laser lipolysis method of the invention comprises detecting thermal or optical radiation from the surface of the patient's skin above the treatment area to prevent damage to the lower dermis of the patient. In addition, a method of the invention includes applying a temperature sensitive material to the patient's skin over the treatment area, the temperature sensitive material indicating a temperature change resulting from harmful temperatures in the lower dermis.

In another aspect, the patient's dermis is cooled externally during laser lipolysis treatment to reduce the temperature rise due to laser radiation from inside the skin. A laser lipolysis system and method of the invention can comprise a contact cooling element that is located on the surface of the patient's skin overlying the treatment area. The contact cooling element can be transparent to allow for the detection of radiation from the surface of the skin above the tip of the fiber. Alternatively, chilled air can be applied to the surface of the skin above the treatment area.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
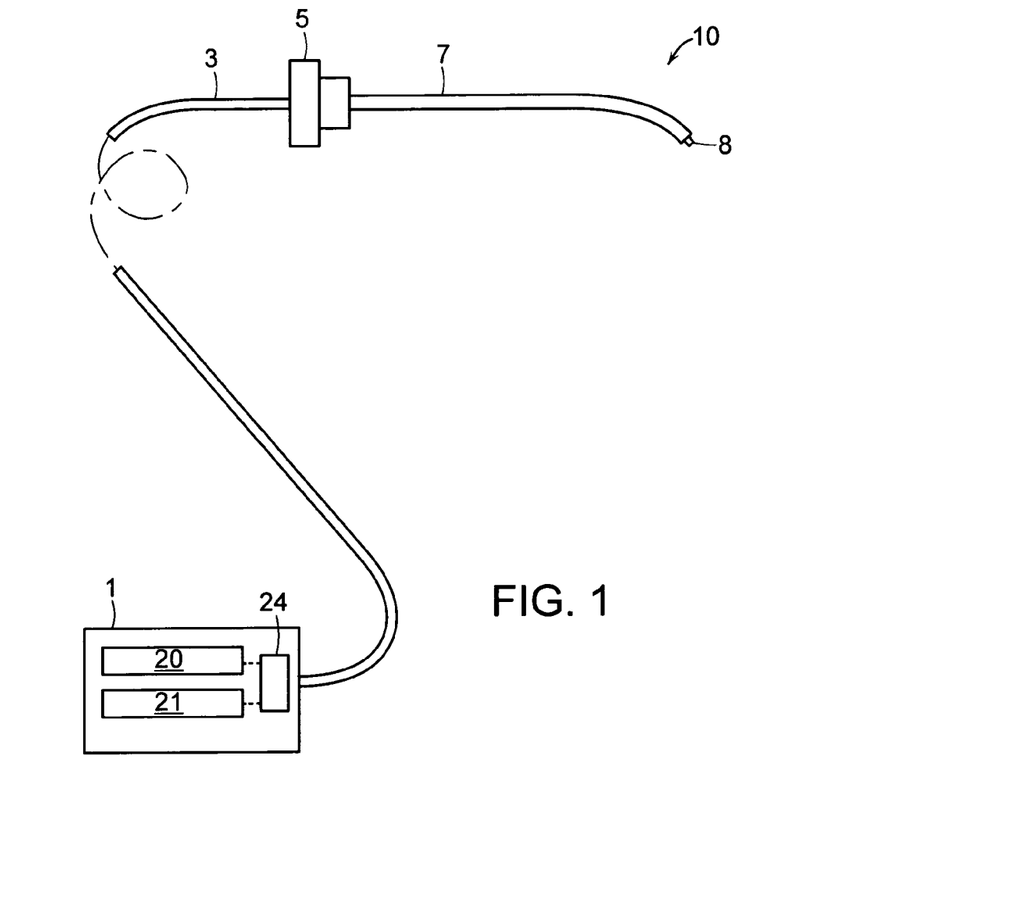
FIG. 1 is a schematic diagram of the laser lipolysis system of the invention.

A description of preferred embodiments of the invention follows. With reference initially to FIG. 1, the device comprises a laser source 1 coupled to an optical fiber 3. The fiber 3 connects to a hollow cannula 7, and extends through the interior of the cannula 7, terminating at or near the cannula tip. Preferably, the proximal end of the fiber 3 protrudes out from the tip of the cannula 7 by approximately 1-2 mm. The fiber 3 can be connected to the cannula 7 using any conventional means, such as a Touhy-Borst connector 5, which holds the fiber tight within the cannula. In operation, laser energy from the source 1 is coupled into the fiber 3, and is conveyed along the length of the fiber to the cannula tip. The laser energy can thus be directed from the end of the fiber to a treatment site by controlling the location and orientation of the cannula tip.

The cannula 7 is a thin, needle-like structure, that is preferably made from stainless-steel. Generally, the cannula has an external diameter of between about 1 to 2 mm. Smaller-diameter cannulas can also be used. The cannula could also be larger, such as the approximately 5 mm-diameter cannulas used in conventional liposuction treatment. The length of the cannula can vary depending upon the particular laser lipolysis application, although typically the cannula will be between about 8 and 10 inches long. In certain embodiments, such as shown in FIG. 1, the cannula 7 includes a curved portion 10 at its distal end, the purpose of which will be described in more detail below.

Optical fiber delivery systems for laser light are well-known. In general, the optical fiber of the present invention has a core diameter of less than about 600 μm, and preferably about 300 μm. The fiber is inserted into and through the cannula 7 at the connector 5 until it exits from the tip of the cannula. The connector 5 typically includes a nut that is tightened against a rubber or elastomeric grommet to secure the fiber in place. As an alternative or in addition to the connector 5 shown in FIG. 1, a larger handpiece connected to the base of the cannula could also be employed.

In the embodiment of FIG. 1, the laser source 1 comprises a treatment laser 20, which in one embodiment is an Nd:YAG laser. The light emitted from the laser 20 is coupled into the optical fiber 3. In this manner, the optical fiber 3 conveys to the point of the cannula 7 a treatment laser beam. The treatment laser 20 emits a beam which is preferably pulsed, at a wavelength between 0.75 and 2.5 μm, for example at 1.06 μm, with an energy level between 30 and 300 mjoules per pulse. The wavelength is preferably between 0.8 and 1.1 μm.

The device described above is used as follows: an entry slit for the cannula is made by inserting a sharp-tip, surgical blade (e.g., a Number 11 blade) through the outer epidermal and dermal layers and into underlying layer of fat tissue. Preferably, the entry slit is about 1 to 2 mm long. It will be understood that the cannula itself can have a sharp tip for forming the entry hole in the patient's skin.

The cannula 7 then is inserted through the entry slit into the subcutaneous layer of adipose cells to be eliminated. The fiber 3 can be pre-loaded into the cannula 7 before the cannula is inserted into the entry slit. Alternatively, the fiber can be fed into the cannula after the cannula has been inserted into the patient. During treatment, the end of the fiber 3 preferably comes directly into contact with the adipose layer. The laser beam, in the appropriate dosage, brings about the rupturing of the membranes of the adipose cells and at the same time cauterizes the very small veins contained in the stroma, which can be easily damaged by the penetration of the cannula 7. In this manner, the adeps becomes liquid and at the same time a local hemostasis is created. The liquefied fat is then absorbed by the body by lymphatic drainage and the action of the phagocytes, while subsequent intervention, similar to that carried out in the case of treatment with ultrasonic probes, to remove the liquefied fat is also possible.

In practice, the cannula 7 is initially inserted subcutaneously and is then moved forward and backward by the operator for the time which is necessary according to the characteristics of the tissue. Typically, to achieve the lipolysis of an adequate quantity of adipose cells, treatment with an energy level of 100 mjoules for a time of 200 microseconds per pulse is appropriate; the needle is kept in each penetration hole for a few minutes. By extracting the cannula and inserting it subcutaneously in an adjacent position, a subsequent portion of tissue is treated. From one and the same entry hole, the cannula 7 can be inserted in various radial directions, treating an entire area of the tissue.

Figure 2:
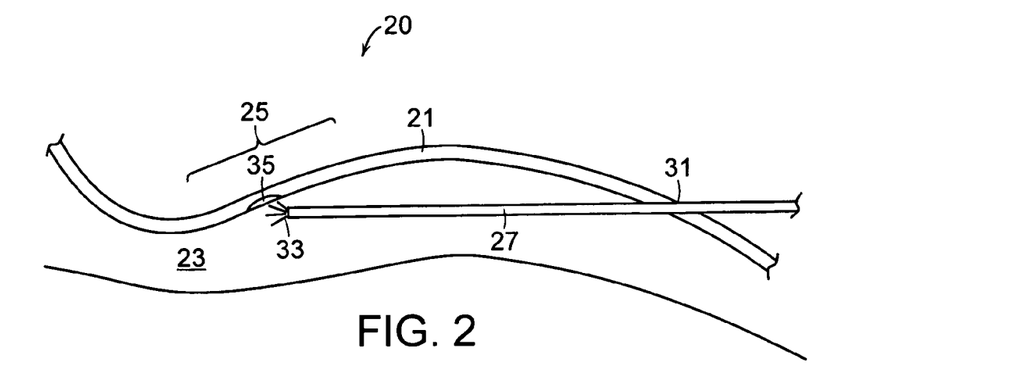
FIG. 2 is a cross-sectional side-view of the treatment area of a patient containing a conventional straight cannula.
Figure 3A:
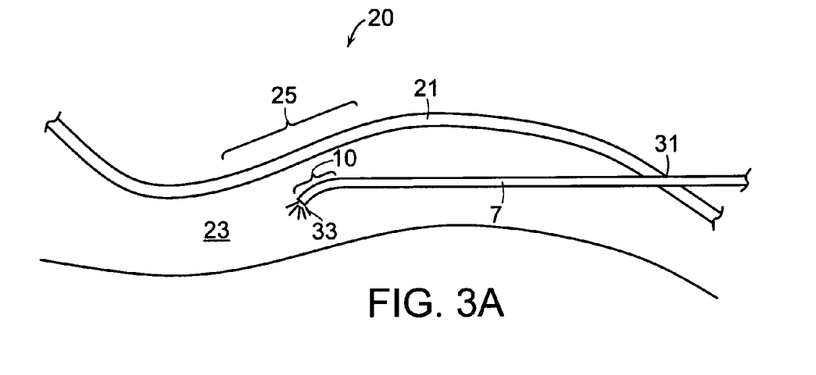
FIG. 3A is a cross-sectional side-view of the treatment area of a patient containing a cannula having a curved portion in accordance with the invention.

As shown in FIG. 1, in one aspect of the invention, the cannula 7 includes a curved portion 10 at is distal end. This curved shape of the cannula advantageously helps direct the treatment laser beam towards the targeted adipose tissue and away from the dermal layers. This is shown more clearly by reference to FIGS. 2 and 3A, which depict a cross-sectional side-view of the treatment area of a patient. In general, the areas of the body most frequently targeted for lipolysis treatment (e.g., hips, legs, abdomen, chin, arms, etc.) comprise contoured, rather than planar, body structures. An example of the type of contoured body structures likely to be encountered during a typical laser lipolysis treatment session is shown in FIGS. 2 and 3A. As shown in these drawings, the treatment area 20 comprises the outer dermal layers 21 and an adipose (fat) layer 23 beneath the dermal layers. The dermal 21 and adipose 23 layers are not flat, planar structures, but have contoured regions, such as curved portion 25.

As shown in FIG. 2, in existing lipolysis techniques, a conventional straight cannula 27 is inserted through entry hole 31, where it can be moved forward and backward by the operator to treat various regions of the adipose layer 23 with laser light. The operator can locate the position of the cannula tip 33 by virtue of an aiming laser, which projects visible light from the cannula tip through the overlying dermal layers 21. However, a deficiency with respect to existing laser lipolysis systems is that the operator has no reliable way for determining the depth of the cannula tip 33 in relation to the dermal layers 21. Thus, as shown in FIG. 2, as the straight cannula 27 is moved towards the curved portion 25 of the treatment area, the cannula tip 33 will quickly (and unknowingly to the operator) approach the underside of the patient's dermal layers 21. This is problematic, since the treatment laser beam, directed at close proximity to the patient's skin, generally contains sufficient energy to cause significant damage to the dermal layers 21. In FIG. 2, for example, the treatment beam emitted from the cannula tip 33 will damage a portion 35 of the dermal layers 21 at the curved portion 25 of the treatment area. Note that the dermis can be damaged even when the tip of the cannula is located entirely within the adipose layer 23. Thus, it is difficult for the operator to know that the laser is damaging the dermal layers, since the operator cannot easily determine whether the cannula tip is too close to the dermis, either by "feel" or by visual inspection of the aiming beam. If sufficient laser energy is directed at the patient's skin, this can result in non-reversible damage to the lower dermis, including damage to the vascular plexus, skin necrosis, and even perforation of the dermis.

Accordingly, in one aspect, the lipolysis system of the present invention comprises a cannula 7 having a curved portion 10, as shown in FIG. 3A. The curved portion 10 is located at the distal end of the cannula, and is preferably shaped to roughly correspond to the contour of a typical body structure encountered during laser lipolysis therapy. As shown in FIG. 3A, for example, the distal end of the cannula 7 has a downward curve, which roughly corresponds to the contoured region 25 of the treatment area. It will be understood that the curved portion can be a gradual curve (as shown in FIG. 3A), or could be a sharper, angular bend. Accordingly, even when the cannula tip 33 is brought into close proximity to the underside of the patient's dermis, the laser energy from the tip 33 is generally directed away from the dermis, and thus avoids injury to the dermal layers. In particular, the curved laser lipolysis cannula of the invention is advantageously able to avoid non-reversible injuries to the lower dermis, including, for example, damage to the vascular plexus.

Figure 3B:
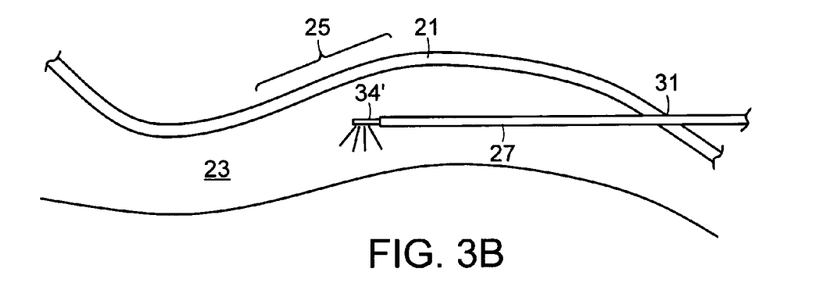
FIG. 3B is a cross-sectional side-view of the treatment area of a patient containing a cannula with a side-firing fiber in accordance with one embodiment of the invention.

In another embodiment, shown in FIG. 3B, a conventional straight cannula 27 is used in conjunction with a side-firing fiber 34 that directs substantially all of the laser energy emitted from the tip of the fiber away from the dermis to minimize damage. Side-firing fibers are well-known in the art, and include, for example, fibers having a small angled mirror at the tip of the fiber, fibers having a polished tip, or any other means to direct the laser output beam in a pre-determined direction. It will also be understood that a side-firing fiber 34 could also be used in conjunction with a cannula having a curved portion, as shown in FIG. 3A.

Figure 4A:
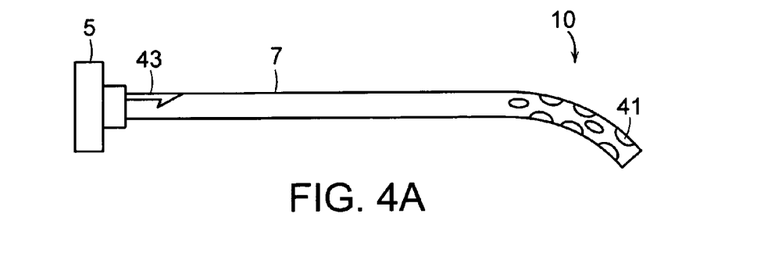
FIGS. 4A and 4B illustrate laser lipolysis cannulas of the invention.
Figure 4B:
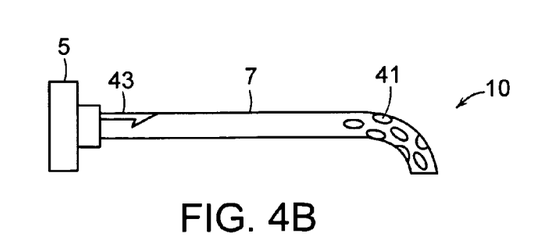

With respect to a cannula having a curved portion, it will be understood that the precise curvature of the curved portion of the cannula is not critical to the present lipolysis system and method. For example, as shown in FIGS. 4A and 4B, a lipolysis system of the invention can include a plurality of different cannulas for treating different body areas. A first cannula (FIG. 4A) can be a longer cannula (e.g. 10 inches) having a curved portion with a longer radius of curvature, while a second cannula (FIG. 4B) can be relatively shorter (e.g., 8 inches) with a shorter radius over the curved portion. The longer cannula may be more advantageous for performing lipolysis treatment over larger areas such as a patient's hip, for instance, while the shorter cannula can be used in tighter areas, such as the patient's chin. In certain embodiments, the radius of the curved portion of the cannula is approximately 6 inches, and is generally between about 1 and 6 inches.

In another aspect, the hollow cannula 7 of the present invention can include side holes 41, as shown in FIGS. 4A and 4B. Side holes 41 are typically present in the cannulas used for conventional liposuction treatment, and are used to help collect and remove fatty tissue from the treatment area. In the present invention, a cannula having side-holes can be used in a combination laser lipolysis/liposuction treatment method. More particularly, the laser energy from the optical fiber is first used to liquefy the adipose cells in the treatment area, and then the liquified fat can be drawn into the cannula through the side holes 41, and removed from the body. A negative pressure can be applied to the cannula, using a vacuum source, for instance, to facilitate removal of the liquified fat cells.

In another aspect, the cannula 7 of the invention includes a visible marker 43 that indicates to the operator the direction of curvature of the curved portion 10. Since during operation, the curved portion is typically located under the patient's skin, the marker 43 assists the user in determining which direction the tip of the cannula is directed. The marker 43 could be, for example, an arrow which points in the direction of curvature of the curved portion. The marker is preferably located at the base of the cannula, or on the connector. In the case of a cannula with a side-firing fiber, as shown in FIG. 3B, the marker 43 can indicate in which direction the fiber emits laser light.

Following the laser lipolysis treatment of the invention, the cannula 7 and optical fiber 3 is then withdrawn from the body through the entry slit. An advantage of the present lipolysis technique, particularly as compared to conventional liposuction techniques, is that the entry slit for the laser cannula can be made so small, no suturing of the slit is required post-treatment.

In the embodiment shown in FIG. 1, the laser source 1 comprises two separate lasers: a treatment laser, and an aiming laser 21, which emits radiation in the visible range. A beam combiner 24 couples the light emitted from each of the lasers 20, 21 into the optical fiber 3. In this manner, the optical fiber 3 conveys to the point of the cannula 7 a treatment laser beam, as well as an aiming beam in the visible range. The aiming laser 21 allows the operator, in reduced ambient light, to follow the position of the end of the fiber under the patient's skin, since the visible light from the aiming laser emitted from the fiber can be seen through the skin. The operator can therefore control the instantaneous point of application of the laser energy generated by the treatment laser 20. Generally, the aiming laser 21 is most effective when used in conjunction with a conventional straight cannula, since the light from the aiming laser 21 may not be visible when employing a curved cannula as shown in FIG. 3A, or with a side-firing optical fiber, as shown in FIG. 3B, which directs the emitted laser light away from the patient's dermis.

Figure 5:
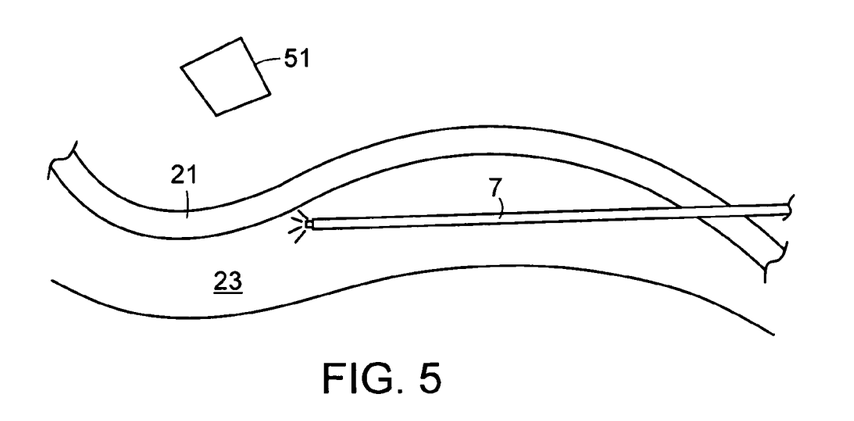
FIG. 5 is a cross-sectional side-view of the treatment area of a patient including a radiation detector above the treatment area.

Turning now to FIG. 5, yet another embodiment of the invention is shown. In this embodiment, a radiation detector 51 is positioned above the treatment area of the patient. Preferably, the detector 51 is aimed to detect radiation from the surface of the skin directly above the subcutaneous cannula tip 33. In certain embodiments, the detector 51 can be physically connected to cannula 7 in such a manner so as to ensure that the detector is properly positioned to detect radiation from the tip of the cannula. For example, the detector 51 can be positioned at the distal end of an arm (not shown), where the base of the arm is connected to the cannula 7 or to the connector 5. In other embodiments, the detector 51 is not connected to the cannula, and the operator positions the detector to detect radiation from the cannula tip 33. The operator can adjust the position and/or orientation of the detector in response to the location on the patient's skin of the visible light from the aiming beam. In one embodiment, the detector 51 can be worn by the operator on a head-strap or other item of headgear (not shown), so that when the operator looks toward the spot of light from the aiming beam, the detector 51 will automatically be aimed toward the cannula tip 33.

In one embodiment, the detector 51 is a temperature sensor that detects the temperature of the skin directly above the cannula tip 33. The detector 51 is programmed to detect a temperature rise in the skin resulting from the tip 33 of the cannula, and thus the treatment laser beam, moving into close proximity to the interior surface of the dermal layer 21. The detector 51 can thus be programmed to warn the operator when the temperature at the surface of the skin has risen to a level that is indicative of potentially harmful temperatures in the lower dermis. Thus, the operator then knows that she is operating too close to the dermis, and can move the cannula 7 back away from the dermal layer.

In an alternative embodiment, the detector 51 is an optical sensor that detects the brightness of the visible light from the aiming laser emitted through the patient's skin. As in the embodiment where the detector is a temperature sensor, an optical sensor can be programmed to warn the operator when the intensity of the aiming beam rises to a level which indicates that the tip of the cannula is too close to the dermis. The operator then knows to move the cannula away from the dermal layer.

Figure 6:
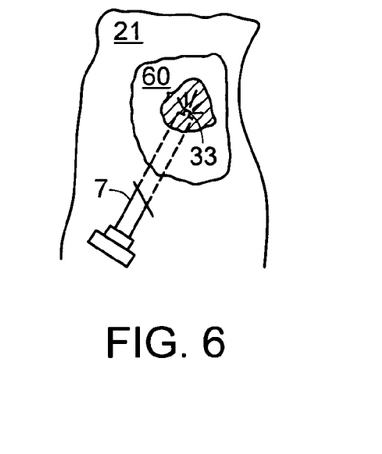
FIG. 6 illustrates a laser lipolysis treatment with a temperature sensitive material being applied to the surface of the patient's skin.

Another embodiment is shown in FIG. 6. In this embodiment, a temperature sensitive material is applied to the patient's skin over the treatment area. As shown in FIG. 6, the cannula 7 is inserted into the patient for laser lipolysis treatment. The application of the relatively high-energy treatment beam within the adipose layer, proximate to the lower dermis, causes the temperature at the surface of the patient's skin to increase. A temperature sensitive material 60 is applied on the surface of the skin 21. The rise in temperature causes a noticeable chemical change to the material 60, such as a change in color (indicated by hatched region in FIG. 6). This change in color warns the operator when the tip of the cannula is too close to the lower dermis, risking dermal injury. Examples of suitable temperature sensitive materials include thermal chromic markers, such as the OMEGALAQ® Temperature Indicating Liquid, from Omega Engineering, Inc, of Stamford, Conn.

It will be understood that the embodiments described in connection with FIGS. 5 and 6 can be used with both conventional straight cannulas, as well as cannulas having curved portions, as previously described herein.

Figure 7:
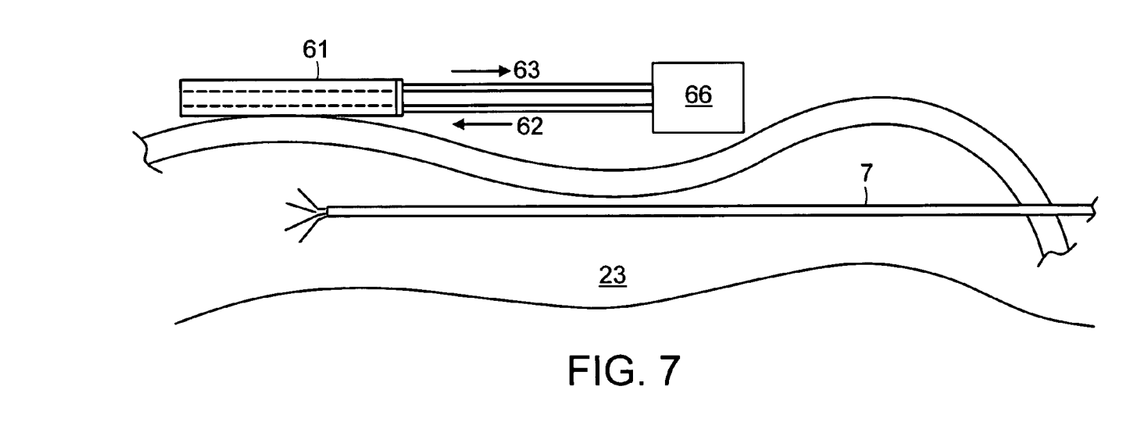
FIG. 7 illustrates a laser lipolysis treatment with a transparent contact cooling element located on the surface of the patient's skin.
Figure 8:
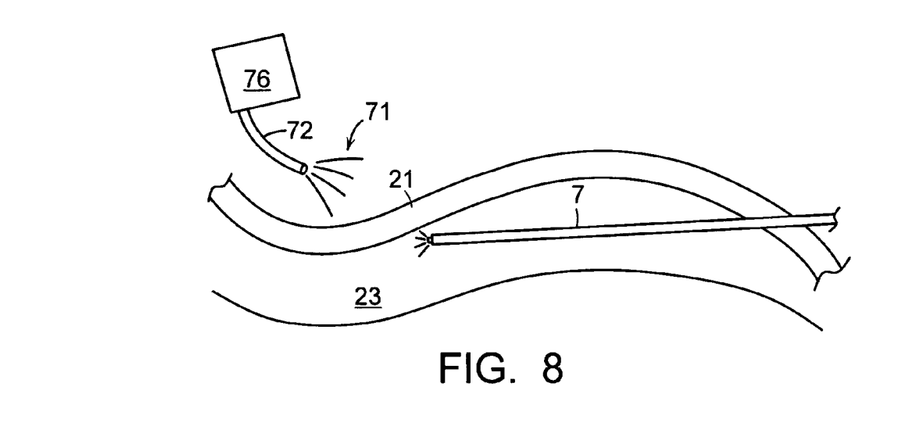
FIG. 8 illustrates a laser lipolysis treatment with chilled air being applied to the surface of the patient's skin.

Turning now to FIG. 7, a laser lipolysis system and method of the invention includes a contact cooling element 61 that is located on the surface of the patient's skin overlying the lipolysis treatment area. The cooling element 61 cools the patient's dermis so as to reduce the temperature rise due to laser radiation from inside the skin, and thereby minimize damage to the patient's dermis. In one embodiment, the contact cooling element 61 is connected to a cooling unit 66 by inlet line 62 and outlet line 63. The cooling unit 66 circulates a cooling fluid through line 62 to the cooling element 61, and back through outlet line 63. The contact cooling element 61 can be made transparent to allow for the detection of radiation from the surface of the skin above the tip of the fiber, as in the embodiment shown in FIG. 5. In an alternative embodiment, shown in FIG. 8, a stream of chilled air 71 can be applied to the surface of the skin above the treatment area, for example, using a cooling unit 76 connected to a hose 72.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for the removal of subcutaneous adipose layers, comprising:
    creating an entry hole on a patient's skin;
    subsequently inserting a blunt tip of a hollow cannula through the entry hole into the subcutaneous adipose layers;
    providing an optical fiber within the cannula, the optical fiber terminating in the vicinity of the blunt tip of the cannula;
    generating a treatment laser beam, the treatment laser beam being conveyed through the optical fiber and into the adipose layers, the wavelength and energy of the treatment beam being selected to cause rupturing of the adipose cells;
    moving the cannula through an area of tissue to deliver the treatment laser beam to liquefy the adipose cells;
    detecting radiation from the surface of the patient's skin above the treatment area, the radiation being indicative of the proximity of the tip of the cannula to the lower dermis of the patient;
    detecting thermal radiation indicative of the temperature of the patient's skin;
    moving the cannula in response to the detected thermal radiation; and
    removing ruptured adipose cells from the subcutaneous adipose layers.

2. The method of claim 1, further comprising generating an aiming laser beam, the aiming laser beam being conveyed through the optical fiber to allow transcutaneous vision of the tip of the cannula, and wherein the detected radiation comprises visible light, the intensity of which is indicative of the proximity of the tip of the cannula to the lower dermis of the patient.

3. The method of claim 1, wherein detecting radiation from the surface of the patient's skin includes detecting radiation directly above the subcutaneous cannula.

4. The method of claim 1, further including placing the optical fiber in direct contact with the adipose layer.

5. The method of claim 1, wherein removing tissue includes removing ruptured adipose cells by drawing them into the hollow cannula.

6. The method of claim 1, wherein removing tissue includes allowing ruptured adipose cells to be absorbed by the body.

7. The method of claim 1, wherein the wavelength of the treatment laser beam is between 0.75 and 2.5 μm.

8. The method of claim 1, wherein the wavelength of the treatment laser beam is between 0.8 and 1.1 μm.

9. The method of claim 1, wherein the wavelength of the treatment laser beam is 1.06 μm.

10. The method of claim 1 wherein creating the entry hole includes creating the entry hole with a blade.

* * * * *